United States Patent
Rullo et al.

(10) Patent No.: US 6,228,026 B1
(45) Date of Patent: May 8, 2001

(54) SURGICAL SUPPORT APPARATUS WITH SPLINED COUPLING, CROSS BAR SUPPORT AND HEAD-TO-TOE EXTENSION FOR SURGICAL RETRACTOR APPARATUS

(75) Inventors: Janice Lee Rullo, Mayfield Heights; William John Koteles, Broadview Heights, both of OH (US)

(73) Assignee: Rultract, Inc., Cleveland, OH (US)

( * ) Notice: Subject to any disclaimer, the term of this patent is extended or adjusted under 35 U.S.C. 154(b) by 0 days.

(21) Appl. No.: 09/373,959

(22) Filed: Aug. 13, 1999

Related U.S. Application Data

(62) Division of application No. 09/224,185, filed on Dec. 31, 1998.
(60) Provisional application No. 60/072,240, filed on Jan. 23, 1998.

(51) Int. Cl.$^7$ .................................................. A61B 17/02
(52) U.S. Cl. .......................................... 600/227; 600/231
(58) Field of Search .................................. 600/231, 228, 600/230, 229, 227

(56) References Cited

U.S. PATENT DOCUMENTS

| | | | |
|---|---|---|---|
| 373,362 | * 11/1887 | Hamilton | 600/228 |
| 1,048,750 | 12/1912 | Smith . | |
| 1,242,688 | 10/1917 | Hawley . | |
| 1,914,202 | 6/1933 | Henze et al. . | |
| 3,403,675 | 10/1968 | Carr . | |
| 3,643,655 | 2/1972 | Peronti . | |
| 3,710,783 | 1/1973 | Jascalevich . | |

(List continued on next page.)

FOREIGN PATENT DOCUMENTS 232451 12/1968 (SU) .

OTHER PUBLICATIONS

Stille Stainless Steel Retractors catalog dated Dec. 18, 1939.
KNY Scheerer Corp., Catalog of Surgical Instruments dated 1959, pp. 70–75 and 90–92.
The Surgical Armamentarium, V. Mueller, dated 1973, pp.68, 281, 346, 347.

(List continued on next page.)

*Primary Examiner*—Paul J. Hirsch
(74) *Attorney, Agent, or Firm*—Renner, Otto, Boisselle & Sklar, LLP

(57) ABSTRACT

A first embodiment of a support system for a surgical retractor device includes a pair of vertically extending support members, releasably attachable to a patient support platform, at least one horizontally extending cross bar attached to and supported by the pair of vertically extending support members, and at least one lifting device disposed on the at least one cross bar and attached for retraction to a retractor assembly. The first embodiment may further include a horizontal extension, upon which may be mounted a lifting device. The first embodiment may further include a second cross bar, upon which a second lifting device may be mounted. A second embodiment of the surgical support system provides an extension for a surgical retractor support device, including an extender bar, a clamp, a first receptacle and a second receptacle for receiving a horizontal support bar from the surgical retractor support device, wherein the first receptacle may be disposed at approximately right angles to the horizontal support bar and the clamp is positioned to retain the horizontal bar in the receptacle. A third embodiment of a support system for a surgical retractor device provides a generally vertically extending support member for a surgical retraction apparatus, and includes a lower portion of the support member having a rectilinear portion for insertion into an anchoring receptacle, an upper portion of the support member having a horizontally extending portion, and a splined coupling adaptor for connecting together the lower and upper portions, wherein the adaptor comprises a splined segment having a key-like splined portion and a lock-like splined portion.

22 Claims, 6 Drawing Sheets

U.S. PATENT DOCUMENTS

| | | |
|---|---|---|
| 3,823,709 | 7/1974 | McGuire . |
| 4,099,521 * | 7/1978 | Nestor et al. .................... 600/231 |
| 4,143,652 | 3/1979 | Meier et al. . |
| 4,151,838 | 5/1979 | Crew . |
| 4,622,955 | 11/1986 | Fakhrai . |
| 4,702,465 | 10/1987 | McConnell . |
| 4,865,019 | 9/1989 | Phillips . |
| 4,971,038 * | 11/1990 | Farley .......................... 600/230 |
| 5,088,472 | 2/1992 | Fakhari . |
| 5,109,831 * | 5/1992 | Forrest ......................... 600/231 |
| 5,876,333 * | 3/1999 | Bigliami et al. ............. 600/231 |

OTHER PUBLICATIONS

The Surgical Armaentarium, American V. Mueller, dated 1980, pp.74, 75, 78, 87, 88.

Codman & Shurtleff, Inc., Catalog for Surgical Products dated 1984, pp.431–437.

Rultract Incorporated, Circulator Applied Internal Mammary Artery Retractor advertisement (undated).

Transaxillary Approach for First Rib Resection to Relieve Thoracic Outlet Syndrome, David B. Roos, M.D., from the Department of Surgery, University of Colorado School of Medicine, Annals of Surgery, Mar. 1966.

Thoracic Outlet Syndrome, David B. Roos, M.D. and J. Cuthbert Owens, M.D., Arch Surg—vol. 93, Jul. 1966.

* cited by examiner

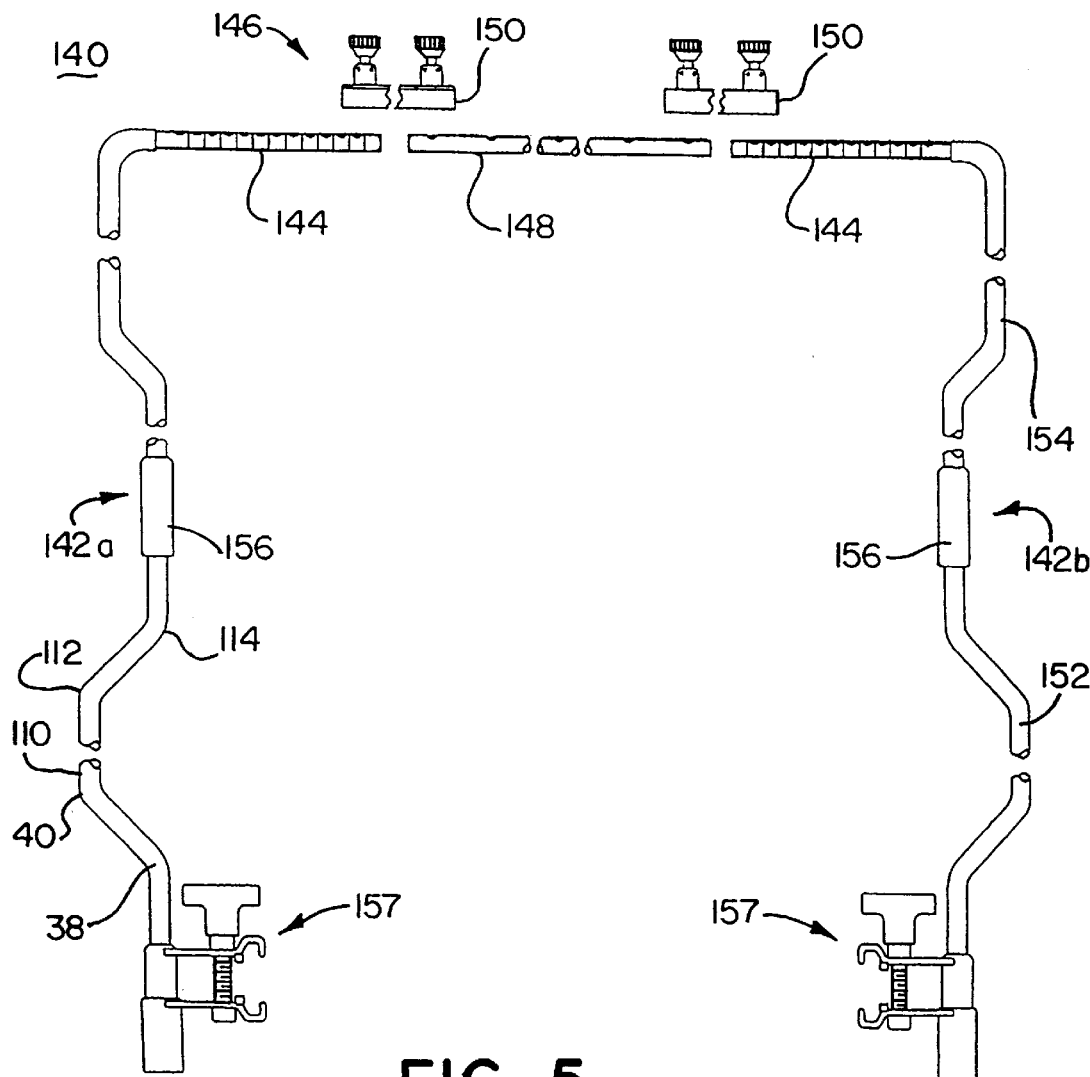
FIG. 5
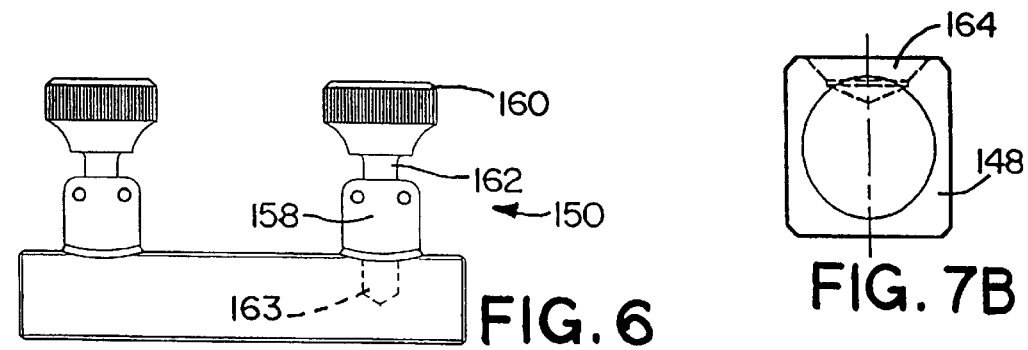
FIG. 6
FIG. 7B
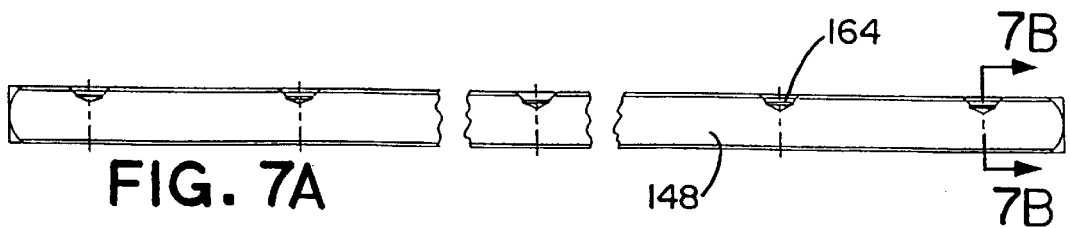
FIG. 7A

SURGICAL SUPPORT APPARATUS WITH SPLINED COUPLING, CROSS BAR SUPPORT AND HEAD-TO-TOE EXTENSION FOR SURGICAL RETRACTOR APPARATUS

CROSS-REFERENCE TO RELATED APPLICATIONS

Reference is hereby made to the following applications copending herewith, the disclosure of each of which is hereby incorporated by reference in its entirety: SURGICAL SUPPORT APPARATUS WITH SPECIALIZED RAKES, Ser. No. 60/072,366; SURGICAL SUPPORT APPARATUS WITH CROSS BAR SUPPORT AND EXTENSION FOR RETRACTOR APPARATUS, Ser. No. 60/072,240; SURGICAL SUPPORT APPARATUS WITH ADJUSTABLE RAKE AND ADJUSTABLE CABLE LIFTING DISK, Ser. No. 60/072,273; and SURGICAL SUPPORT APPARATUS WITH A Z-SHAPED RAKE PLATE, Ser. No. 60/072,274. The present application is a divisional of Ser. No. 09/224,185 filed Dec. 31, 1998 which claims priority to U.S. Provisional application Serial No. 60/072,240 filed Jan. 23, 1998.

FIELD OF THE INVENTION

The present invention relates generally to surgical instruments for holding and elevating body parts and/or for maintaining a clear opening to a body area during surgery, particularly thoracic surgery. More specifically, the present invention relates to support apparatus upon which surgical devices, such as retractors and the like, may be operably mounted.

BACKGROUND OF THE INVENTION

In the performance of surgery in the chest cavity, generally referred to as thoracic surgery, it is desirable to hold open the surgical cavity to provide access to the organ or body part upon which the surgery is being performed. This is especially important in the case of cardiac surgeries. An early example of a surgical retractor for use in coronary bypass surgical procedures which include dissection of the internal mammary artery is disclosed in U.S. Pat. No. 4,622,955, which is incorporated by reference.

In the device of U.S. Pat. No. 4,622,955 plural rakes which engage the body and retract the surgical cavity formed by a midsternotomy are relatively fixedly positioned with respect to each other from a rod. The rod may be elevated or lowered, as desired. However, there is no adjustment for the rakes relative to the rod, to each other or to the surgical cavity. Furthermore, the rakes are generally small, having sharply pointed tips and are generally designed to be employed in pairs for the purpose of retracting one side of a sternum which has been split by a midsternotomy. The device of U.S. Pat. No. 4,622,955 cannot provide the support required for other procedures which have been recently developed as alternatives to the midsternotomy approach to the coronary bypass, and it is not adapted for use in reoperative midsternotomy procedures.

It is well known and appreciated that in surgical procedures, time is of the essence, and delays associated with adjustments of support equipment are unwanted. Additionally, during certain procedures, it may be desirable to impose or to change a biasing force on a body portion which is undergoing a surgical procedure or treatment. Further, it is desirable to minimize the number of personnel required to assist in performance of a surgical procedure, to minimize the number of personnel who must enter the sterile field, and to minimize the tasks, such as holding a retractor, of personnel during surgical procedures. Further, it is desirable to have available to the surgeon instruments appropriately adapted to each type of procedure.

Coronary Bypass Surgery: The Midsternotomy

Coronary bypass surgery, in which the internal mammary artery is harvested from the chest wall and used for anastomosis of a vessel to bypass poorly functioning coronary arteries, has been performed thousands of times and has become an almost routine procedure for cardiac surgeons. Since the inception and throughout the development of the procedure, coronary bypass surgery has required a midsternotomy to provide access to the heart and coronary arteries. In the midsternotomy, an initial incision is made from the manubrium of the sternum to a point toward the xiphoid. Next, the sternum is split down the middle by means of a reciprocating sternal saw in order to provide access to the coronary arteries and the internal mammary artery. It has been estimated that in 1988, some 350,000 midsternotomy procedures were performed for coronary bypass surgery.

In performing the coronary bypass procedure, following the midsternotomy, it is necessary to retract one side of the split sternum in order to gain access to the thoracic cavity, and particularly to the internal mammary artery. Either the left or right internal mammary artery may be harvested for the bypass, so either side of the chest may need to be retracted. Retractors have been developed in order to provide the requisite retraction of the split sternum. An early example is disclosed in U.S. Pat. No. 4,622,955. The RUL-TRACT® internal mammary artery retractor is a more advanced retractor which has been developed to provide left or right internal mammary artery exposure in the undersurface of the chest wall. The RULTRACT™ internal mammary retractor has been extensively used in coronary bypass surgery. The RULTRACT® retractor is not limited to coronary bypass surgery, having been used in various other thoracic surgical procedures, such as lung reduction and pericardial drainage.

The RULTRACT® internal mammary retractors include a rake plate and two or possibly three rakes. Most frequently, in use the two rakes are applied to one side of the opening formed by a midsternotomy and the rake plate is attached to a lifting device. The lifting device lifts the rake plate and the rakes, applying an upward and outward retraction to the sternum by which the surgical cavity is opened. The sternum is securely held in the open position when the lifting device is locked in position. This exposes the entire course of the mammary artery from its origin to its bifurcation, allowing its dissection. The rakes in the conventional retractor have a relatively small radius of curvature and have quite sharp tips to provide a secure attachment to the sternum. With the sternum securely held in the open position, the coronary artery dissection may then be carried out by the surgeon. In the standard midsternotomy, the retractor provides good exposure and allows the surgeon sufficient access for the dissection of the mammary artery.

After the coronary artery has been harvested, the RUL-TRACT® retractor is removed and a sternal retractor is placed in the chest and the grafting and anastomoses is performed. Closure is normally accomplished in this procedure by applying wires or staples to the sternum to hold it together in the properly aligned position for healing.

The midsternotomy is a highly invasive procedure, and much of the difficulty in recovering from a coronary surgical procedure involving a midsternotomy is due to the trauma resulting from the midsternotomy rather than to any trauma inflicted upon the coronary arteries or other thoracic organs and structures. As a result, a need has been identified for a less invasive procedure which will provide the surgeon with access to the coronary and internal mammary arteries with a minimum of trauma to the thoracic region.

The Mid-Cab, A Less Invasive Procedure

A less invasive procedure which has been developed to provide access to the mammary artery and the coronary arteries for coronary bypass surgery is known as the mid-cab or minimally invasive technique. In the mid-cab, an incision is made between the third and fourth rib, in the third intercostal space. The fourth rib is released from the sternum, and the incision is retracted downward by attaching a retractor rake to the fourth rib. A second retractor rake is next attached to the third rib, which is retracted upward and in the cranial direction. With access thus provided to the third rib and in the direction of the upper chest, the surgeon is able to create an opening from the third rib to the first rib or subclavian region. Via this opening, the surgeon is provided with access to the mammary artery, which is progressively dissected from the chest wall as the opening is progressively advanced toward the first rib. With the development of this procedure, a need has been identified for more advanced retractors specially adapted to the mid-cab procedure, and particularly for a retractor which can simultaneously retract the third and fourth ribs in different directions.

It is well known among cardiac surgeons that the position of the internal mammary artery in the chest is variable from patient to patient. For this reason, during the mid-cab procedure, it is sometimes necessary for the surgeon to manipulate the chest wall to provide adequate access to the mammary artery. The surgeon may have to either elevate or depress the chest wall in the region of the first rib in order to gain access to the mammary artery so that it can be dissected in this procedure. Thus, a need has been identified for devices which can assist the surgeon in the less invasive mid-cab procedure, particularly including a retractor capable of two-direction retraction at the site of the intercostal incision and devices for providing elevation and/or depression of the clavicle and first rib region of the chest wall.

Reoperative Coronary Bypass Surgery

As coronary surgery has become increasingly prevalent and postoperative coronary rehabilitation more successful, a larger number of patients are surviving longer than the expected patency of their graft conduits. This has resulted in an increasing number of patients having to undergo a second coronary bypass procedure. The second, or reoperative, procedure has sometimes been referred to as a "re-do" procedure. Unfortunately, the re-do midsternotomy is neither as simple nor as safe as the initial procedure. This is primarily due to the scarring and resultant adhesions which develop between the internal side of the sternum and the underlying organs and tissues of the thoracic cavity following the initial midsternotomy. When the re-do midsternotomy is performed by essentially repeating the steps of the initial procedure, an increase in morbidity and mortality has been observed. Thus, a need has arisen for an alternative procedure.

An alternative procedure which has been adapted to coronary surgery in order to avoid the dangers of the re-do midsternotomy is known as a xiphoid entry. In the xiphoid entry, an initial incision is made along the scar from the previous midsternotomy to a point midway between the xiphoid and the umbilicus. The old sternal wires are removed. The xiphoid process is excised. A single retractor rake is applied to the caudal end of the sternum and the sternum is firmly retracted in an anterior and cranial direction. This allows the surgeon to directly visualize the anterior retrosternal space, so that the retrosternal adhesions can be taken down. The surgeon progressively takes down the adhesions toward the subclavian, until the sternum is freed from the underlying organs. Once this is done, the retractor may be removed and the sternum divided with a reciprocating sternal saw as in the original procedure.

During the retraction particular care must be exercised since, first, the quite sharp rake tips of the standard retractor are applied directly to the lower end of the sternum from which the xiphoid process was excised, and second, a very strong lifting force is required to elevate the entire sternum. The possibility of unintended trauma to the sternum exists. A second problem which has been experienced with the procedure described above is that the entire retractor plate and the extra, non-used rake must be suspended in a central location in the operating field, further obstructing the work area with its already limited space available. A third problem is that due to the rake plate and various parts attaching it to the lifting apparatus, the retraction force applied to the sternum is not transmitted in a simple straight line from the lifting apparatus to the sternum. Thus, a need has been identified for a rake which is more appropriately adapted to the xiphoid entry in a re-do coronary bypass procedure.

In the procedures described in the foregoing and in additional thoracic surgical procedures, the surgeon may be required to adapt the support apparatus for retraction of the patient's body in several directions at once. In such an instance, a single retractor held by a single support device may not be sufficient to provide the retraction required by the surgeon. Furthermore, it may be helpful to the surgeon to combine various embodiments of retraction devices in order to adequately obtain the retraction required.

Accordingly, there is a strong need in the art to provide for surgical retractor apparatus with which to facilitate the development and implementation of new surgical procedures, particularly less invasive procedures such as the mid-cab coronary artery bypass procedure, and for more radical thoracic procedures, such as a lung reduction or other procedure.

SUMMARY OF THE INVENTION

The present invention, in one embodiment, provides a cross bar support assembly, which extends across the operating table on which the patient lies during the surgical procedure, and upon which a plurality of lifting and retracting devices may be mounted. In one embodiment of the cross bar assembly, the cross bar is a unitary bar attached to a pair of novel support members and suspended across the operating table. In a second embodiment of the cross bar assembly, the cross bar comprises two conventional retractor support arms which are connected to each other across the operating table by a novel arrangement of couplings and extension bars attached to the horizontal portion of the retractor supports.

In an embodiment of the present invention, there is provided a support system for a surgical retractor device which includes a pair of vertically extending support members, releasably attachable to a patient support platform, such as an operating table, a horizontally extending cross bar, attached to and supported by the pair of vertically extending support members. The cross bar preferably extends across the operating table. The support system further includes at least one ratcheting lifting device, which is disposed on the cross bar, and is attached to a retractor assembly for retraction. In one embodiment of the cross bar system, each of the vertically extending support members is a conventional retractor support apparatus, and the cross bar includes an extension attached thereto. Preferably, the extension includes coupling devices for attaching to the horizontal portions of the conventional support apparatus. In a second embodiment of the support system, each of the vertically extending support members is a slotted member not having a horizontally extending support portion, and the cross bar is a member supported by the pair of vertically extending support members. In both embodiments, at least one ratcheting lifting device is disposed upon the cross bar.

The embodiment mentioned in the preceding paragraph may further include a second horizontally extending cross bar, attached to and supported by the pair of vertically extending support members. The second cross bar may have mounted thereon one or more ratcheting lifting devices. The second cross bar, as well as the first cross bar, may include a horizontally extending extension, disposed at an angle to the cross bar, upon which a ratcheting lifting device may be disposed. The extension mounted on the second cross bar preferably includes an extender bar portion, a clamp portion, and a first receptacle for receiving the horizontal support bar from the surgical retractor support device, wherein the receptacle is disposed at approximately right angles to the horizontal support bar and the clamp is positioned to retain the horizontal bar in the receptacle. Preferably, the extension extends at a right angle to the cross bar, but other angles are possible within the scope of the present invention. The second cross bar, like the first, may include a plurality of further ratcheting lifting devices, mounted on the cross bar or upon one or more extension bars.

In another embodiment of the present invention, a support pole for a retractor support system is provided with a splined coupling, by which the exact angle at which the retraction device is suspended with respect to the "head-to-toe" direction of the patient's body may be selected and reliably retained without the possibility of slippage. The splined coupling provides for adjustment of the angle during the course of a surgical procedure, thereby allowing the surgeon to better adapt to the changing conditions and needs of the patient.

More particularly, in the embodiment of the present invention mentioned in the previous paragraph, there is provided a generally vertically extending support member for a surgical retraction apparatus which includes a lower portion of the support member having a rectilinear portion for insertion into an anchoring receptacle, an upper portion of the support member having a horizontally extending portion, and a splined coupling adaptor for connecting together the lower and upper portions, in which the adaptor comprises a splined segment having lock- and key-like splined portions. The splines may be involute. Preferably the key-like splined segment is disposed on the lower portion of the support member. Alternatively, the key-like splined segment may be disposed on the upper portion of the support member. Preferably, each splined segment comprises at least 12 teeth, but more preferably each splined segment comprises at least 19 teeth.

In still another embodiment of the present invention, a right-angled extension bar for a retractor support system is provided, providing a novel and much improved adaptability to the configuration of the retractor support system, thereby allowing the surgeon to better adapt to the changing conditions and needs of the patient during surgery.

More particularly, in the embodiment of the present invention mentioned in the preceding paragraph, there is provided an extension for a surgical retractor support device, which includes an extender bar portion, a clamp portion, and a first receptacle for receiving a horizontal support bar from the surgical retractor support device, in which the receptacle is disposed at approximately right angles to the horizontal support bar and the clamp is positioned to retain the horizontal bar in the receptacle. Preferably, the extension includes the extender bar being horizontally disposed when the horizontal bar is in the receptacle. Preferably, the first receptacle is disposed in the clamp portion. Preferably, the receptacle is disposed in the clamp portion and the clamp portion comprises a second receptacle for receiving the horizontal support bar, and wherein the second receptacle is disposed collinearly with the horizontal support bar. Preferably, a cross section of the extender bar is rectilinear, and more preferably it is square.

The present invention provides devices which may be selected and quickly implemented as required in an individual surgical procedure depending on the particular patient's needs. The system allows the surgeon to perform a less-invasive procedure while maintaining the option to easily switch to the more radical surgical procedures, such as the midsternotomy, in the event of unforeseen difficulties. When the RULTRACT® retractor system and the device of the present invention are employed, the surgeon is provided with a greatly improved degree of adaptability in the procedures chosen during a particular surgical procedure, with a minimum change of retraction apparatus.

To the accomplishment of the foregoing and related ends, the invention then comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 5 is a side elevational view of another embodiment of the cross bar support assembly in accordance with the present invention partially dismantled;

FIG. 6 is a side elevational view of a coupling device for use in the embodiment illustrated in FIG. 5;

FIG. 7A is a side elevational view of an extension bar for use in the embodiment illustrated in FIG. 5;

FIG. 7B is a cross-sectional view taken at line B—B of FIG. 7A;

DETAILED DESCRIPTION

Figure 1:
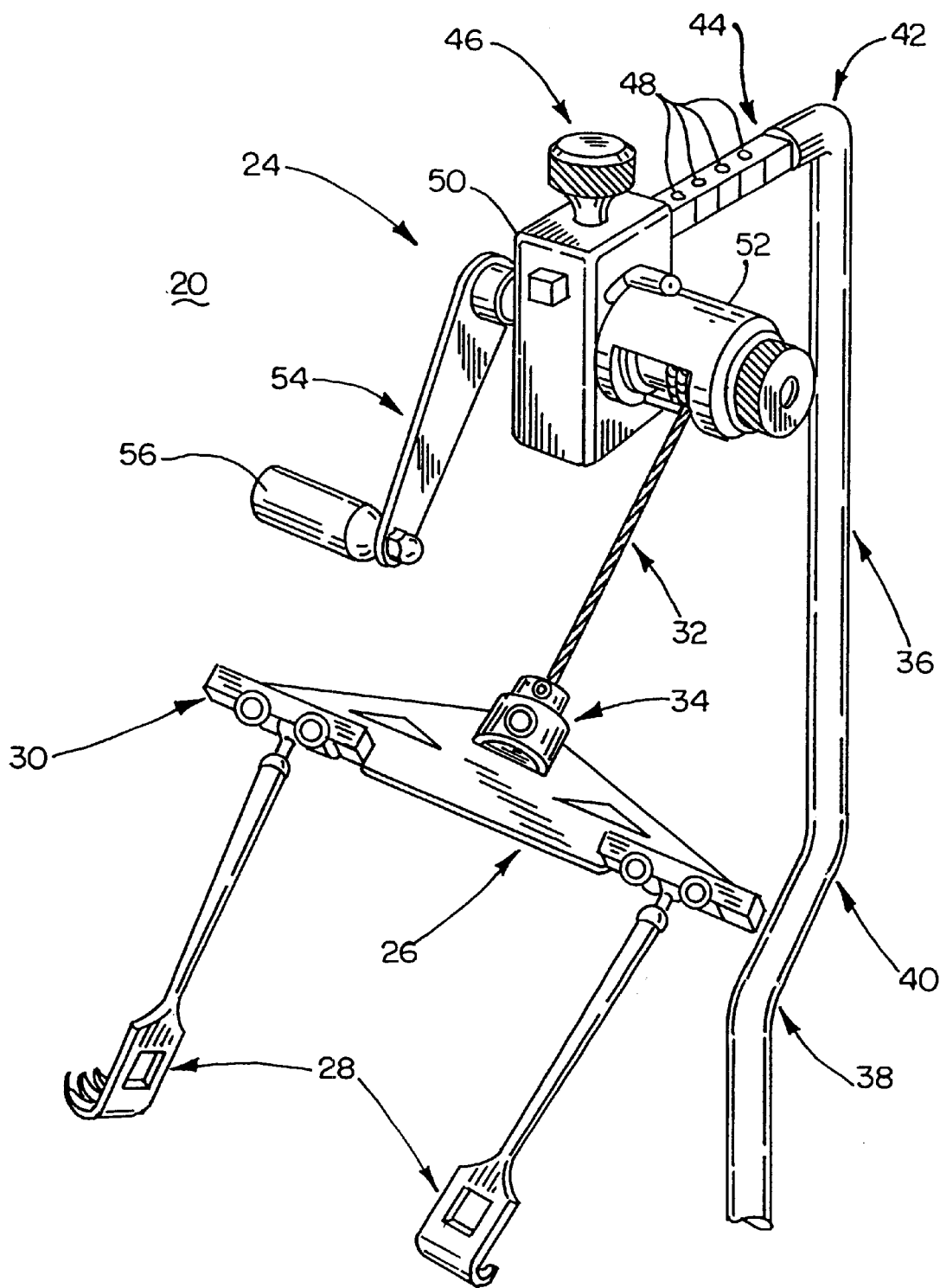
FIG. 1 is a perspective view of a conventional Rultract® surgical retractor.

The present invention will now be described with reference to the drawings wherein like reference numerals are used to refer to like elements throughout. As mentioned above, the present invention relates to surgical instruments for holding open a body part during surgery, for example, to maintain open and clear a surgical cavity during surgery, particularly including cardiac surgery or other thoracic surgery. In all embodiments described hereinafter, the preferred material of construction is stainless steel, preferably 304 stainless steel, which has good strength and sterilization characteristics and is resistant to corrosion even after many cycles of use, cleansing and sterilization.

Referring to FIG. 1, a conventional RULTRACT® retractor and surgical support assembly 20 are shown. The RULTRACT® retractor includes a lifting device 24, a rake plate 26, at least one rake 28 for applying retraction to a patient's body, and pivoting mounting means 30 for mounting the rakes 28 to the rake plate 26. The rake plate 26 is attached to the ratcheting lifting device 24 by a cable 32. The cable 32 is attached to the rake plate 26 by a pivot hub connector 34.

The rake plate 26 and the rakes 28 associated therewith may be raised or lowered via the cable 32, which is connected to the lifting apparatus 24. As described below the RULTRACT® system preferably includes a ratcheting lifting device 24, although other lifting devices could be used. Preferably a pivot hub connector 34 allows the rake plate 26 to rotate relative to the cable 32 to facilitate positioning of the rakes 28 relative to the surgical cavity of the patient without twisting the cable 32, which could result in a torque applied to the retractor rake plate 26, which undesirably could be transmitted to the patient's body.

In the conventional RULTRACT® retractor assembly 20, the ratcheting lifting device 24 is mounted on a support pole 36. Although not shown in FIG. 1, the support pole 36 is mounted at its lower end to a surgical table by conventional means. Preferably, the support pole 36 includes bends 38 and 40 which dispose outward the portion of the support pole 36 which is above the level of the surgical table so as to provide additional space in the surgical field around the patient. At the upper end of the pole 36, is a preferably right-angled bend 42 connecting the support pole 36 to a horizontally extending portion 44. The horizontally extending portion 44 extends outwardly above the patient, so that the retraction force is applied at least partially in an upward direction. Since the lifting device 24 is not aligned with the patient's midline, the retraction is applied partially outwardly laterally with respect to the patient.

In this embodiment, the lifting device 24 is mounted on the horizontal extension 44. The lifting device 24 is provided with a securing bolt 46 by which the lifting device 24 is securely positioned on the extension 44. To facilitate quick and sure positioning of the lifting device 24 on the extension 44, a plurality of bores 48 are provided, into which an end of the securing bolt 46 may be inserted. The bores 48 allow for precise horizontal adjustment of the position of the lifting device 24 relative to the patient and the surgical field.

The ratcheting lifting device 24 preferably includes a ratcheting winch assembly 50 for reeling in the cable 32. The cable 32 is attached to and preferably is reversibly wrapped around a spool (not shown) extending outwardly from the winching assembly 50. The spool around which the cable 6 wraps is preferably partially enclosed by a housing 52. The opposite rend of the spool is attached to, and the winching assembly is actuated by, the crank arm 54 and crank handle 56, in conventional fashion.

In the following description of the present invention, like reference numbers refer to like parts. The lifting device and support arm used in the present invention are preferably essentially the same as the conventional assembly described above and will not be further described except as necessary to indicate the functioning of the present invention relative thereto.

Figure 2:
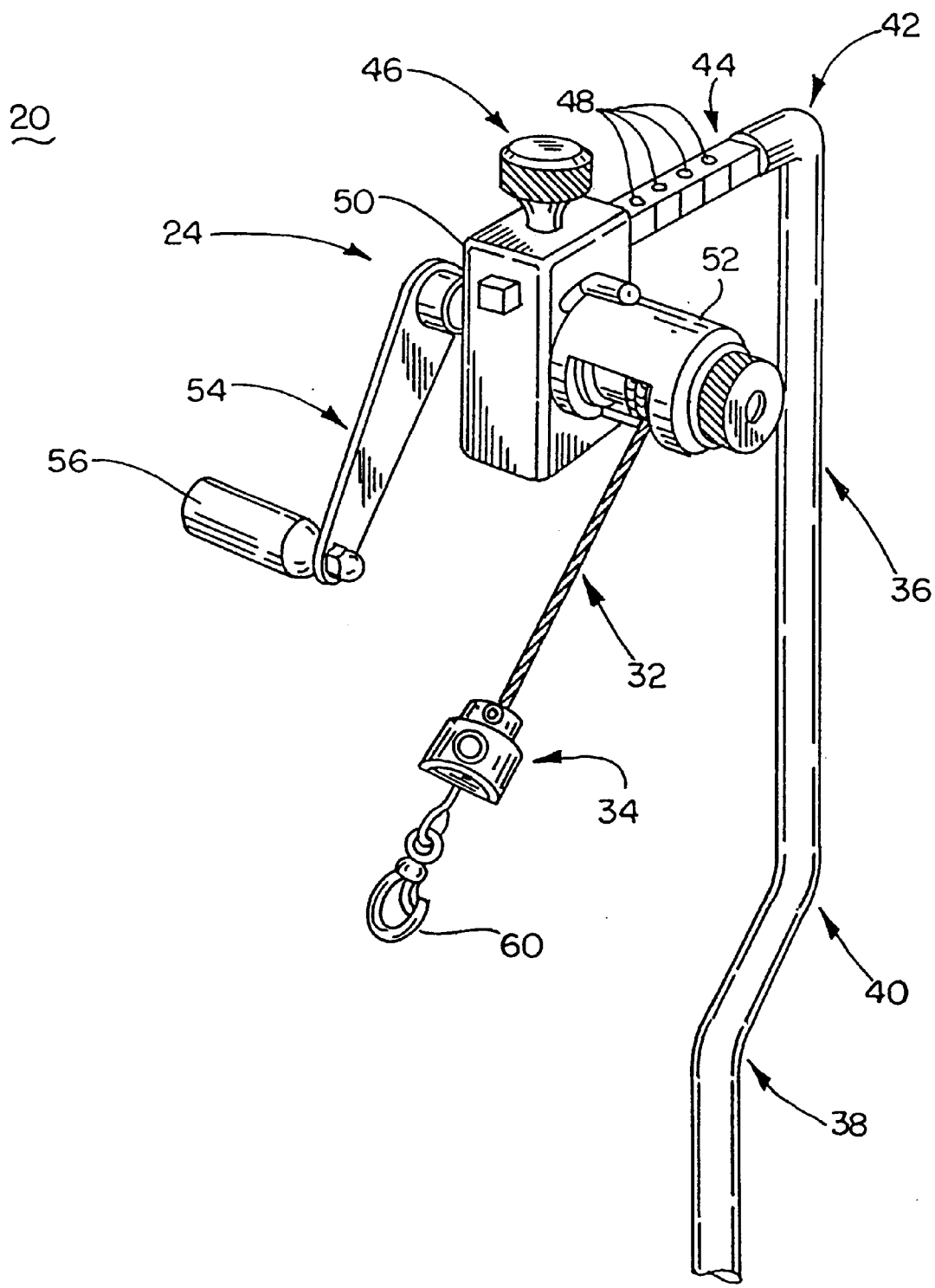
FIG. 2 is a perspective view of a conventional Rultract® retractor support and lifting apparatus with a swiveling hub and snap clip for attaching a rake plate or individual rakes.
Figure 3A:
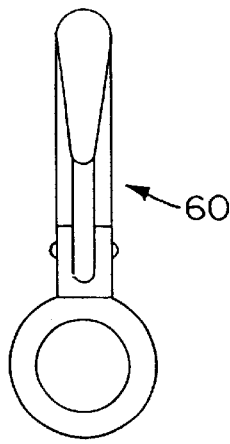
FIGS. 3A and 3B are respectively front and side elevational views of a snap clip as used in an embodiment of the present invention.
Figure 3B:
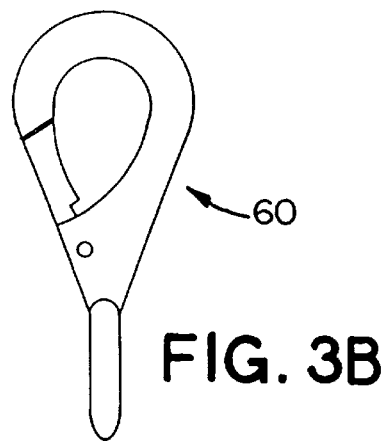

Preferably, in the present invention, the ratcheting lifting device 24 is similar to the ratcheting device 24 shown in FIG. 1 and available from RULTRACT, INC., Cleveland, Ohio. Referring to FIG. 2, in an alternative embodiment of the surgical support assembly of the present invention, the ratcheting lifting device 24 has the cable 32 attached thereto, as described above with reference to FIG. 1. As shown in FIG. 2, the free end of the cable 32 may have attached thereto a pivot hub connector 34 and a snap ring 60. The snap ring 60 is preferably used for attaching the rakes or retraction apparatus to the cross bar assembly of the present invention. The snap ring 60 provides a secure, but quickly releasable attachment between the lifting device 24 and the rakes or retraction apparatus used with the present invention. FIGS. 3A and 3B show respectively front and side elevational views of the snap clip 60 shown in FIG. 2, and which is exemplary of such a quick-release device which may be used in accordance with the present invention. Other quick-release devices known in the art may be substituted for the snap ring 60.

Similarly, the support bar 36, including the horizontal extension 44, as shown in FIGS. 1 and 2, is the starting point both for one embodiment of the first preferred embodiment of the present invention, a cross bar assembly which employs couplings and an extension bar, and for a second preferred embodiment of the present invention, a "head-to-toe" extension bar which extends at right angles from the horizontal extension 44. The support pole 36 may also incorporate the third preferred embodiment of the present invention, a splined coupling for a support bar. All of these preferred embodiments are described in more detail below.

Figure 4:
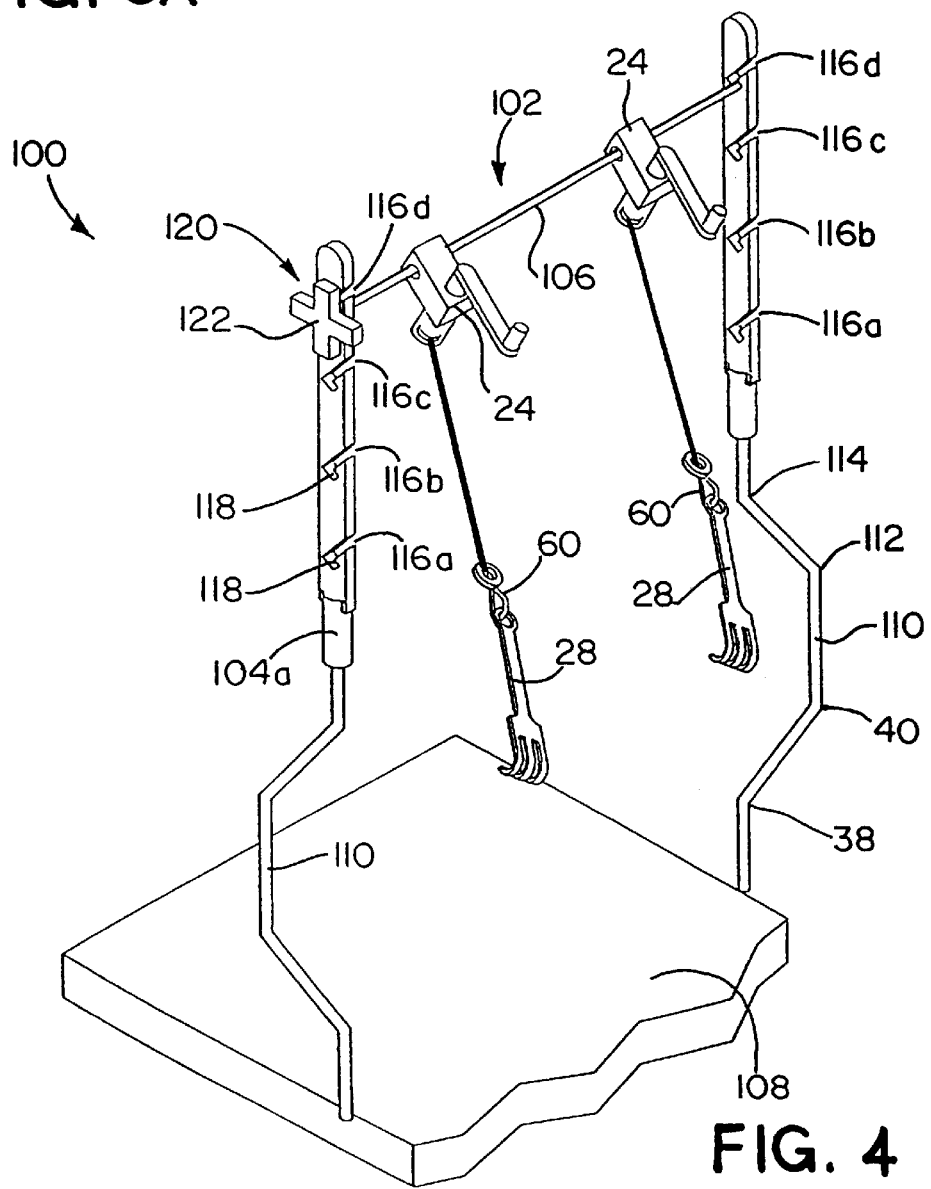
FIG. 4 is a perspective view of a cross bar support assembly in accordance with the first preferred embodiment of the present invention.

In FIG. 4 a cross bar support system 100 is shown including a cross bar assembly 102, which includes vertical support members 104a and 104b and a cross bar 106. The cross bar assembly 102 is mounted on a patient support platform 108, which may be, for example, an operating table. The cross bar assembly 102 includes a horizontally extending cross bar 106. In FIG. 4, the cross bar 106 is shown with two ratcheting lifting devices 24 mounted on the cross bar. The preferred ratcheting lifting devices 24 are the same as those shown in FIGS. 1 and 2, which are commercially available from RULTRACT, INC., Cleveland, Ohio. Of course, other equivalent ratcheting lifting devices may be substituted for the preferred devices, if such equivalent devices are capable of being mounted on the cross bar assembly 102. Further, any number of ratcheting lifting devices 24 may be mounted on the cross bar 106, as needed for a given surgical procedure, and limited only by the space available on the cross bar 106. The ratcheting lifting device 24 may be attached for retraction either to a retractor assembly, such as a rake plate 26 with a plurality of rakes 28, such as shown in FIG. 1, or to a single retractor rake 28, as shown in FIG. 4.

Referring still to FIG. 4, the cross bar 106 is attached to and is supported by the pair of vertically extending support members 104a and 104b, such that the cross bar 106 preferably extends across a patient support platform 108. The vertical support members 104a and 104b are essentially identical, except that they are mirror images of each other. Each vertical support member 104a and 104b includes an outwardly extending portion 110 similar to the outward curve resulting from the bends 38 and 40 shown in FIGS. 1 and 2 and described above. Like the support apparatus in FIGS. 1 and 2, the outwardly extending portion 110 shown in FIG. 4 includes bends 38 and 40. However, unlike the apparatus shown in FIGS. 1 and 2, in the preferred embodiment of the cross bar assembly 102 shown in FIG. 4, the outwardly extending member 110 includes additional bends 112 and 114, by which the vertical support members 104a and 104b are shifted inwardly back to the approximately same vertical position of the lower attached portion of the members 104a and 104b. The outwardly extending portion 110 provides additional stability to the support members 104a and 104b.

In an alternate embodiment, the vertical support members do not include the additional bends 112 and 114, so that the upper portion of the vertical support remains further outboard relative to the patient support platform 108, by a distance determined by the bends 38 and 40. In another alternate embodiment, the vertical support members do not include any outwardly extending portion, so that there are no bends such as the bends 38, 40, 112 and 114 of this embodiment.

The support members 104a and 104b are each releasably attachable to the patient support platform 108. The attachment means are not shown in FIG. 4, but may generally be any conventional attachment device, such as a compression clamp, as used for clamping other support bars and other surgical equipment to the operating table.

As is apparent from FIG. 4, the cross bar support system 100 is quite stable, due to the cross bar 106 connecting together the support members 104a and 104b. Accordingly, it is not necessary that the support members be attached to the platform 108 by a device which restricts the rotation of the support members, such as will be described below in relation to another embodiment of the present invention. An example of a clamping device by which the vertical support members may be attached to the operating table or other patient support system is shown in FIG. 5 and described below.

Referring again to FIG. 4, the cross bar member 106 is made from metal stock which is polygonal in cross-section, having at least two opposing, parallel flat sides. For example the stock may be square, rectangular, hexagonal or octagonal. In one embodiment, the stock is about ½ inch by ½ inch square (about 12.5 mm×12.5 mm). In coordination therewith, the ratcheting lifting devices 24 include a square opening of appropriately matching size so that the devices 24 can be mounted on the cross bar 106. Thus, for example, the opening in the device 24 may be approximately 12.6 mm square, to accommodate some slight variation in the size of the cross bar 106, but to avoid any excess of free movement. It is noted that while the preferred stock is square, other configurations may be used, such as triangular, pentagonal, hexagonal, or rectangular for example. Furthermore, when a term such as "square" is used, this refers to the overall cross-sectional shape, rather than to a perfectly square (or other) cross-section. Thus, a square stock may have slightly rounded corners, for example, and still be considered square.

As shown in FIG. 4, the vertical support members 104 each include a plurality of slots 116a, 116b, 116c and 116d. Although four such slots 116 are shown on each support member 104, any suitable number may be selected, and the invention is not limited to a particular number of such slots.

As shown in FIG. 4, each slot 116 is cut into the vertical support member 110 at a downward angle, so that the force of gravity assists in retaining the cross bar member 106 in the slot. As shown in FIG. 4, the slots 116 preferably include an inset 118, into which the cross bar 106 fits to provide additional stability and security to the cross bar support system 100. Alternative embodiments include, for example, a slot initially disposed substantially horizontally which connects to a downwardly-cut inset 118. The downwardly-cut inset 118 may be angled downward at any angle.

Each slot 116 includes parallel flat sides spaced apart to snugly to accommodate the cross bar 106. Thus, each slot 116 is appropriately sized so that the cross bar member 106 can slide into the slot but is not allowed to rotate within the slot. For example, if the cross bar member is a 12.5 mm square, then the slot is approximately 12.6 mm wide, to accommodate some slight variation in the size of the cross bar member, but to avoid any excess freedom of movement.

The cross bar assembly 102 further includes at least one clamping device 120 for retaining the cross bar on the support member 104. Preferably the clamping device 120 is a compression clamp, by which the handle 122 may be turned to preferably threadingly actuate the clamping device to firmly hold the cross bar 106 to one of the support members 104a or 104b.

In the embodiment shown in FIG. 4, the cross bar assembly 102 utilizes the clamp 120 to hold the cross bar 106 to the support member 104a. Preferably the cross bar 106 is not clamped to the second vertical support member, in FIG. 4 the vertical support member 104b. In an alternative embodiment, the cross bar 106 may be clamped to the other support member, 104b. The cross bar assembly 102, when utilizing the clamp 120 to hold the cross bar 106 to the support member 104a (for example) preferably is not clamped to the second vertical support member 104b.

An embodiment of the cross bar 106 not having a second clamp allows the cross bar to be repositioned by a single surgical assistant working from one side of the surgical support platform 108. This arrangement provides additional flexibility to the use of the cross bar support system 100.

In the above single-clamp embodiment, the non-clamped end of the cross bar 106 is horizontally retained in the slot 116 by an enlarged head (not shown) disposed on the end of the cross bar 106. Thus, the enlarged head on the end of the cross bar 106 which extends through the vertical support member 104b to the outer side of the member 104b, is on the opposite end of the cross bar 106 from the claim 120.

Alternatively, within the scope of the invention, the cross bar 106 may include a second clamping device 120 for holding the cross bar 106 to the support member 104b, if such is deemed necessary to provide additional stability to the cross bar support system 100.

In a second embodiment of the cross bar support system, each of the pair of vertically extending support members is a conventional retractor support apparatus such as that shown in FIGS. 1 and 2. In this second embodiment, the cross bar is not a single bar extending across the patient support platform 108, but preferably includes an extension bar and clamping devices by which the extension is attached to the horizontally extensions of the vertical supports. An example of such an embodiment is shown in FIG. 5.

As shown in FIG. 5, an alternate embodiment of a cross bar support system 140 includes two vertically extending members 142a and 142b, both of which include horizontal extensions 144.

In FIG. 5 is shown a cross bar support system 140 including a cross bar assembly 146. The cross bar assembly 146 shown in FIG. 5 includes two horizontal extensions 144, an extender bar 148, and two dual clamps 150. In FIG. 5, no ratcheting lifting devices 24 are shown, but any number may be mounted on the cross bar assembly 146, as needed for a given surgical procedure, and limited only by the space available on the cross bar assembly 146. The ratcheting lifting devices 24 may be mounted on any or all of the horizontal extensions 144 and the extender bar 148.

The preferred ratcheting lifting devices 24 are the same as those shown in FIGS. 1 and 2, which are commercially available from RULTRACT, INC., Cleveland, Ohio. Of course, other equivalent ratcheting lifting devices may be substituted for the preferred devices, if such equivalent devices are capable of being mounted on the cross bar assembly 146 as described herein. The ratcheting lifting device 24 may be attached for retraction either to a retractor assembly, such as a rake plate with a plurality of rakes or to a single retractor rake, as shown in FIG. 4 for the first embodiment of the cross bar support system 100.

As mentioned above, the cross bar support system 140 includes a pair of vertical support members 142. As shown in FIG. 5, the horizontal extensions 144 are integrally attached to and supported by the pair of vertically extending support members 142. In alternative embodiments the horizontal extensions 144 may be separate parts, appropriately attached to the vertically extending supports 142a and 142b. The horizontal extensions 144 extend horizontally outward above a patient support platform (not shown in FIG. 5, but similar to the patient support platform 108 shown in FIG. 4). The vertical support members 142 are essentially identical to each other. In the preferred embodiment of the vertical support member, each member 142 comprises a lower section 152 and an upper section 154, connected by a coupling 156. The coupling 156 preferably couples by means of a key and lock arrangement, in which the sections interlock to provide a secure attachment of the lower portion 152 and the upper portion 154. In this embodiment, all upper portions 154 are preferably identical and all lower portions 152 are preferably identical, as a result of which each can be mounted on either side of the patient support 108. In one embodiment the coupling 156 is a splined coupling as described in greater detail below.

As shown in the embodiment of FIG. 5, each vertical support member 142 preferably includes an outwardly extending portion 110 similar to the outwardly extending portion 110 shown in FIG. 4 and described above. In the support apparatus shown in FIG. 5, the outwardly extending portion 110 is in the lower section 152 so as to provide additional space in the surgical field near the patient. The outwardly extending portion 110 includes the bends 38 and 40 and the bends 112 and 114. Thus, the coupling 156 of the vertically extending member 142 is approximately vertically above the part of the lower section 152 adjacent an attachment means 157. The outwardly extending portion 110 adds stability to the support members 142.

In an alternate embodiment, the vertical support members may include no additional bends 112 and 114, so that the outwardly extending portion of both the upper section 154 and the lower section 152, and the coupling 156, remain further outboard for the entire vertical height of the vertical support members 142. In another alternate embodiment, the vertical support members include no outwardly extending portion, so that there are no bends such as the bends 38, 40, 112 and 114 of the preferred embodiment. Other combinations may be possible as well.

The support members 142 are releasably attachable by the attachment means 157 to the patient support platform (not shown in FIG. 5), such as an operating table. The attachment means 157 is shown in FIG. 5 as a standard compression clamp for attachment to a rail disposed on most patient support platforms. The clamp may generally be any conventional attachment device, as would be used for clamping vertical support bars and other surgical equipment to the patient support platform.

As is apparent from FIG. 5, the cross bar support system 140 is quite stable, primarily due to the firm attachment to the patient support platform and the attachment through the horizontal extensions 144, the extender bar 148 and the two couplings 150, connecting together with the support members 142 to form a unitary assembly. Accordingly, it is not necessary that the support members be attached to the platform 108 by a device which restricts the rotation of the support members, such as the splined coupling which will be described below in relation to another embodiment of the present invention. However, having the horizontal supports 144 aligned by means of a rotation-restricting device will simplify setting up the cross bar assembly 146.

In one embodiment, the horizontal extensions 144 and the extender bar 148 are made from metal stock which is square in cross-section. In one embodiment, the stock is about ½ inch by ½ inch square (about 12.5 mm×12.5 mm). In coordination with this embodiment, both the clamps 150 and the ratcheting lifting devices 24 include a square opening of appropriately matching size so that the clamps 150 and the devices 24 can be easily and reliably mounted on the horizontal extensions 144 and the extender bar 148. Thus, for example, both the opening in the clamp 150 and the opening in the device 24 may be approximately 12.6 mm square, to accommodate some slight variation in the size of the cross bar member, but to avoid any excess freedom of movement. It is noted that while the preferred stock is square, other configurations may be used, such as triangular, pentagonal, hexagonal, or rectangular for example. Furthermore, when a term such as "square" is used, this refers to the overall cross-sectional shape, rather than to a perfectly square (or other) cross-section. Thus, a square stock may have slightly rounded corners, for example, and still be considered square.

The coupling 150 is shown in more detail in FIG. 6. The coupling 150 includes a pair of locking devices 158 actuated by a handle 160. Preferably, the locking devices 158 are threadingly actuated, such that appropriately rotating the handle 160 extends or withdraws a shaft 162 thereby pressing a shaft tip 163 (shown in phantom in FIG. 6) against a bar inserted into the coupling, resulting in securely positioning the bar in the coupling, or in releasing the bar. In this embodiment the shaft tip 163 is tapered and sized to fit into a bor 164 as shown in FIG. 7A.

The extender bar 148 is shown in FIGS. 7A and 7B. The extension bar 148 is appropriately dimensioned in the length and cross-sectional dimensions to coordinate with the horizontal extensions 144 of the vertical supports 142 when the supports are mounted on a standard patient support platform. Of course, various lengths of the extender bar 148 may be made available to make it possible to use the cross bar assembly on various widths of patient support platform. As shown in FIGS. 7A and 7B, the extension bar preferably includes the regularly spaced bores 164, similar to the bores 48 shown in FIGS. 1 and 2. Similarly, the horizontal extensions 144 preferably include such regularly spaced bores 164.

FIG. 7B, which is a cross-sectional view taken at line B—B of FIG. 7A, shows a cross section of such a bore 164. Preferably, the locking device 158 on the coupling 150 includes the lower end 163 on its threaded shaft 162 appropriately sized and configured to fit into each of the bores 164.

The cross bar assembly 146 is assembled by inserting the horizontal extensions 144 into one side of the couplings 150, and inserting the extension bar 144 into the other end of each coupling 150, and tightening the pair of locking devices 158 on the couplings, such that the shaft tip 163 of the shaft 162 is inserted into one of the bores 164. The cross bar assembly 146 is thereby assembled to form the cross bar support system 140.

Figure 8:
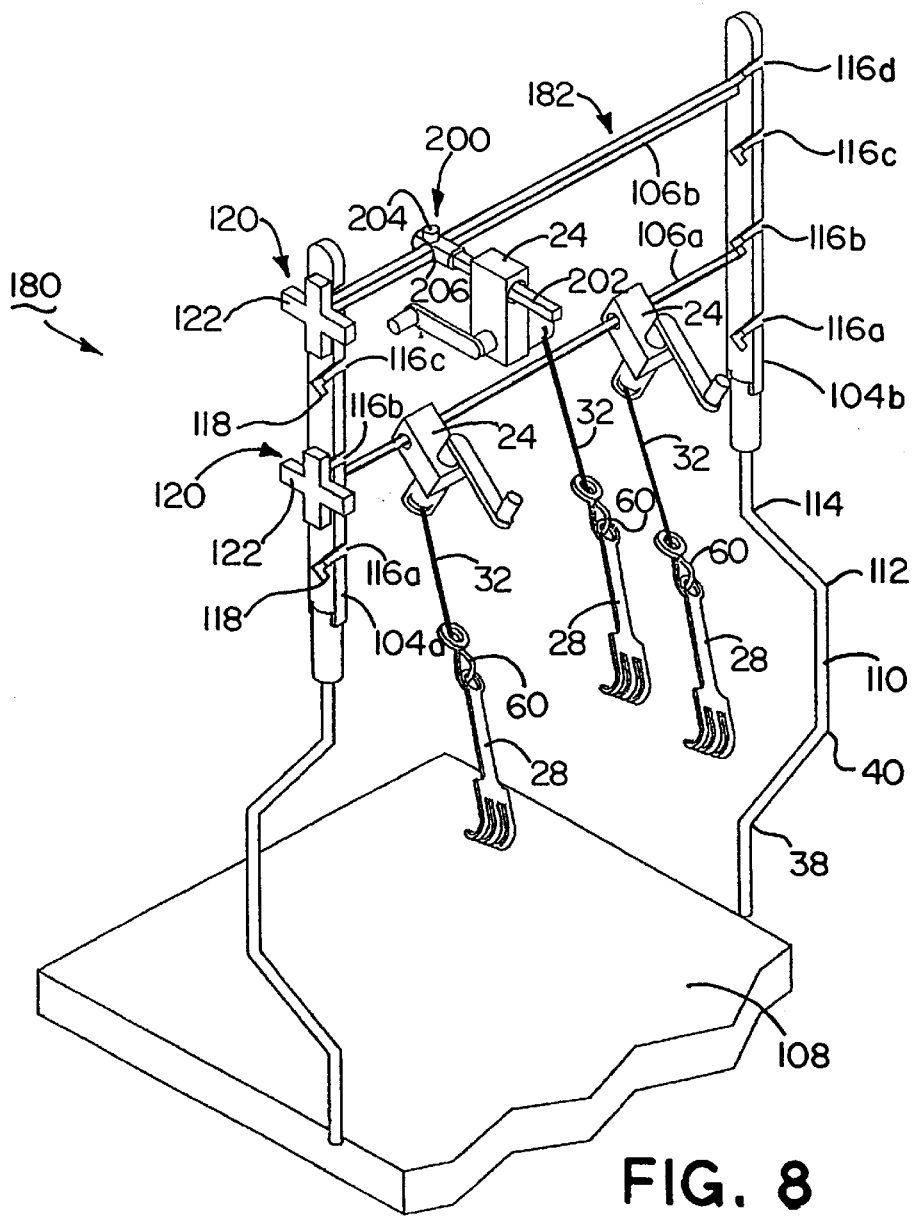
FIG. 8 is a perspective view of a second cross bar support assembly in accordance with the first preferred embodiment of the present invention.

Referring now to FIG. 8, an embodiment of the present invention in the form of a cross bar support system 180 is shown, which includes a cross bar assembly 182 having a first cross bar 106a and a second cross bar, 106b. The second cross bar 106b is attached to and supported by the pair of vertically extending support members in the same manner as described for the cross bar 106 shown in FIG. 4. The second cross bar 106b may be mounted either above or below the first cross bar 106a, and may be mounted in any available pair of the plurality of slots 116a, 116b, 116c and 116d on the vertical support members 104a and 104b.

In the cross bar assembly 182 shown in FIG. 8, the second cross bar 106b may have mounted thereon one or more ratcheting lifting devices 24. Although FIG. 8 shows a ratcheting lifting device 24 mounted on an extender bar 148 rather than directly on the second cross bar 106b, such a device 24 would be mounted thereon in the same manner as described above with respect to the ratcheting lifting devices 24 mounted on the cross bar assembly 200 shown in FIG. 4.

As shown in FIG. 8, the cross bar assembly 182 may include a horizontally extending extension 200, upon which a ratcheting lifting device 24 may be disposed. Although not shown in FIG. 8, more than one extension 200 may be mounted on either the first cross bar 106a or the second cross bar 106b. Similarly, an extension 200 may be mounted on the cross bar 106 of the cross bar assembly 102 shown in FIG. 4.

As described in more detail below with respect to FIG. 9, the extension 200 mounted on the second cross bar 106b preferably includes an extender bar portion 202, a clamp portion 204, and a first receptacle 206 for receiving the cross bar 106b of the cross bar assembly 182, in this example.

Preferably, the extension 200 extends at a right angle to the cross bar. However, other angles are possible where such is helpful to provide flexibility in the angle at which the retractor apparatus is suspended with respect to the patient. Such other angles are within the scope and contemplation of the present invention. In order to provide such an angle, the first receptacle 206 need be disposed at an angle other than a right angle to the longitudinal direction of the extender bar portion 204.

Referring to FIG. 8, the cross bar assembly 182 utilizes the clamps 120 to hold the cross bars 106a and 106b to the support member 104a (for example). As described above for the embodiment shown in FIG. 4, preferably the cross bars 106a and 106b are not clamped to the second vertical support member 104b. Alternatively, either or both of the cross bars 106a and 106b may be clamped to the other support member, 104b. The embodiment of the cross bar 106a and/or 106b which is not provided with a second clamp allows the cross bar to be repositioned by a single surgical assistant from one side of the surgical support platform 108, thus providing additional flexibility to the use of the cross bar support system 180. In this preferred embodiment, the non-clamped end of the cross bar 106a and/or 106b is horizontally retained in the slot 116 by an enlarged head (not shown) located on the end of the cross bar 106 extending through the vertical support member 104b to the outer side of the member 104b. Alternatively, within the scope of the invention, either or both cross bar 106a and 106b may include a second clamping device 120 for holding the cross bar to the support member 104b, if such is deemed necessary to provide additional stability to the cross bar support system 180.

The second cross bar 106b, like the first cross bar 106a, may include a plurality of further ratcheting lifting devices 24, mounted on either of the cross bars, or upon one or more extension bars 200 mounted on either of the cross bars. It is noted that additional cross bars 106 may be mounted on the cross bar assembly 200 or 180, limited only by the number of slots 116. In turn, the number of slots 116 is limited only by the length of the vertical extension 104 and considerations of strength and utility.

The following describes various methods by which the cross bar may be put to use in a surgical procedure. The steps are generally outlined, and are not intended to limit the many uses to which the invention may be put.

In one embodiment, the present invention provides method of providing surgical retraction to a patient positioned relative to a support platform, including the steps of: (1) mounting a pair of vertically extending support members with respect to the platform; (2) mounting a cross bar to the pair of vertically extending support members; (3) mounting a lifting device on the cross bar; and (4) applying retraction to the patient. In one embodiment, the step of mounting a lifting device further includes attaching the lifting device to a retractor assembly. In one embodiment, the step of mounting a lifting device further includes attaching the retractor assembly to an anatomical part of the patient. In one embodiment, the method includes mounting a second cross bar to the pair of vertically extending support members, and may further include mounting a lifting device on the second cross bar for applying additional retraction to the patient.

Figure 9:
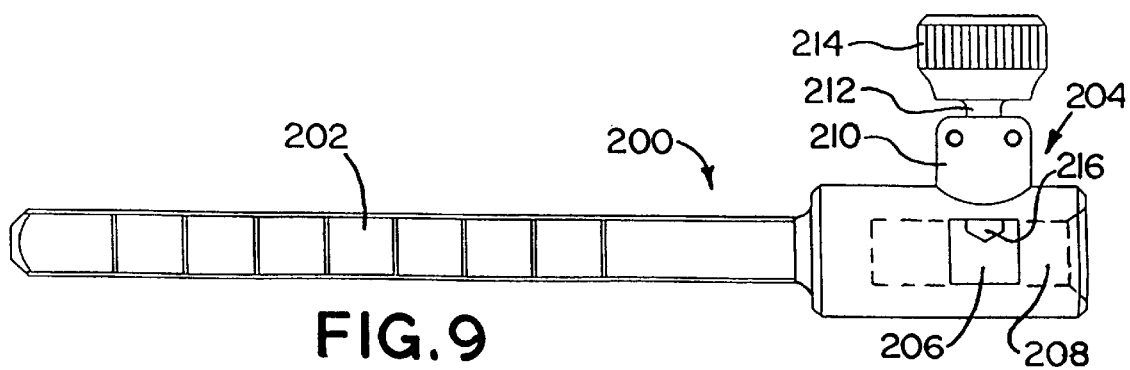
FIG. 9 is a side elevational view of a "head to toe" extender in accordance with a preferred embodiment of the present invention.

In the second preferred embodiment of the present invention, and as shown in FIG. 9, a right-angled extension bar 200 for a retractor support system is provided. The horizontal extension of a vertically extending support, such as the horizontal extension 144 shown in FIG. 5, normally extends outward in a direction transversely across the patient's body. When the right-angled extension bar 200 of the present invention is attached to the horizontal extension 144, the extension bar 200 is oriented parallel with the patient's body, i.e., in a head to toe direction. Accordingly, the right-angled extension bar 200 of the present invention has been referred to as a "head to toe" extension. As a result of the head to toe extension 200, the surgeon is provided with a further novel and improved adaptability in configuring the retractor support system. Thereby, the surgeon may better adapt to the changing conditions and needs of the patient during surgery.

The head to toe extension 200 extends from a device for mounting a ratcheting lifting device 24 or other surgical devices which can be mounted on such bars as have been disclosed in the foregoing descriptions of the preferred embodiments of the invention. The head to toe extension 200 preferably has a ratcheting lifting device 24 or other devices mounted thereon.

As shown in FIG. 9, the head-to-toe extension 200 includes a bar portion 202, a clamp portion 204, a first receptacle 206, and a second receptacle 208. Both the first receptacle 206 and the second receptacle 208 are configured for receiving a horizontal support bar, such as that shown in FIGS. 1, 2 or 5, from the vertically extending support device 36 or 142, respectively. As shown in FIG. 9, the first receptacle 206 is disposed to receive the horizontal support bar at a right angle to the longitudinal axis of the head to toe extension. The first receptacle 206 is similarly sized and dimensioned to receive the cross bar 106 or the cross bars 106a or 106b.

As is shown in FIG. 9, the second receptacle 208 is disposed to receive the horizontal support bar collinearly with the longitudinal axis of the bar 202, and thus to act as a simple extension of the horizontal support.

The clamp portion 204 includes a clamp body 210, a preferably threaded shaft 212, and a handle 214. Preferably, the lower end (opposite the handle) of the shaft 212 is configured to securely fit into a positioning bore such as the bore 164 shown in FIGS. 7A and 7B. The clamp 204, as shown in FIG. 9, is advantageously positioned to retain the horizontal bar in either the first receptacle 206 or the second receptacle 208. A shaft tip 216 on the threaded shaft 212 interacts with the bores 164 to retain the horizontal bar in the clamp 204. It will be noted that while the horizontal bar can only be inserted a short distance into the second receptacle 208, the horizontal bar can be inserted any desired distance into the first receptacle 206, since the first receptacle 206 is an opening which passes completely through the clamp 204.

In one embodiment, a cross section of the bar 202 is rectilinear. In another embodiment, the bar 202 is square. The bar 202 should be the same size as the horizontal extending portions 44 and 144 and the cross bars 106, 106a and 106b, described with respect to the other embodiments of the present invention.

The following describes various methods by which the extension may be put to use in a surgical procedure. The steps are generally outlined, and are not intended to limit the many uses to which the invention may be put.

In one embodiment, the present invention provides a method of providing surgical retraction to a patient, a portion of which is positioned relative to a support platform, including the steps of: (1) mounting with respect to the support platform a generally vertically extending support member; (2) mounting with respect to the vertically extending support member an extension, the extension including an extender bar; (3) mounting a lifting device on the extender bar; and (4) applying retraction to the patient. In one embodiment, the extension includes a receptacle and the step of mounting the extension includes placing a portion of the vertically extending support member into the receptacle. In one embodiment, the extension includes a clamp disposed in relation to the receptacle and the step of mounting the extension includes retaining the portion in the receptacle with the clamp. In one embodiment, the receptacle is disposed to receive the portion at approximately right angles to the extender bar. In one embodiment, the vertical support member has a horizontally extending portion, and the step of mounting the extension includes mounting the extension on the horizontally extending portion.

Figure 10:
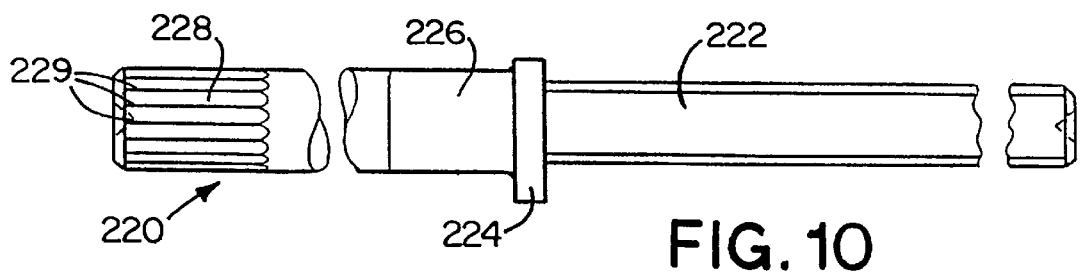
FIG. 10 is a side elevational view of an embodiment of a support pole having a splined segment and a square segment.

The third preferred embodiment of the present invention is generally illustrated in FIGS. 10–14. As shown in FIG. 10, a lower section 220 for a vertical support member for a retractor support system is provided. The lower section 220 includes a base segment 222, a radially extending shoulder 224, a main segment 226, and a splined segment 228.

Preferably the lower section 220 is machined from a single piece of stock, but may also be made by welding together appropriately sized and shaped pieces. Preferably, the base segment 222 is generally square in cross-section, and is appropriately sized and adapted to fit into an anchoring receptacle having a standard compression fitting and a standard device for clamping attachment to a patient support platform such as an operating table (not shown). In a standard device, a clamp, such as the device 166 shown in FIG. 5, may be integrally provided on the base segment 222 for attachment to a standard-sized bar or rail extending from the side of the patient support. The device may alternately include a standard compression fitting having a square opening for receiving the base segment of items such as IV holders and other equipment which may be used during a surgical procedure. The base segment 222 of the lower section 220 is sized appropriately to fit into the square opening of the standard compression fitting. The base segment 222 may have any desired length, but preferably is at least about one foot (30 cm) in length, to allow for an adequate range of vertical adjustment of the vertical support member.

The base segment 222 abuts a radially extending shoulder 224, which effectively establishes a minimum height at which the vertical support can be mounted. The base segment 222 may be raised and clamped into position by the compression fitting, but it cannot be lowered any further than allowed by the shoulder 224.

The portion of the lower section 220 above the shoulder 224 is the main segment 226. The main segment 226 may have any cross-sectional shape, but is preferably round in cross-section. The main segment 226 is preferably in the range from about 1 to about 2 feet in length (about 30 cm to about 60 cm), but it may be longer or shorter as required for a particular application. The main segment is preferably machined from stock having a diameter in the range from about ½ inch to about ½ inch (about 12 mm to about 25 mm). The radially extending shoulder 224 preferably has a slightly larger diameter than the main segment 226, but may have the same diameter, as long as the diameter or width of the shoulder 224 is larger than the width of the opposite sides of the square base segment 222.

The main segment 226 includes the splined segment 228. The splined segment 228 has a plurality of teeth 229. Preferably the splined segment 228 has at least 12 teeth 229, and more preferably the splined segment has 19 such teeth. The splined segment 228 is preferably machined from the same stock from which the main segment 226 is made. Therefore, the teeth 229 of the splined segment will normally extend radially outward no further than the diameter of the main segment 226.

Figure 11:
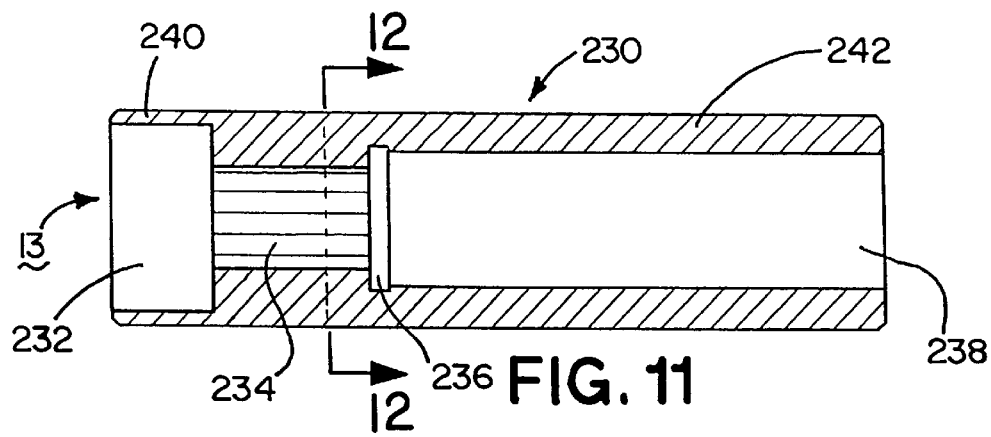
FIG. 11 is an longitudinal cross-sectional view, taken at line 11—11 of FIG. 13 of a coupling device including a coupling spined segment.
Figure 12:
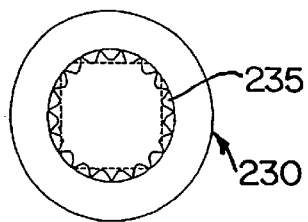
FIG. 12 is an axial cross-sectional view taken at line 12—12 of the coupling device shown in FIG. 11.
Figure 13:
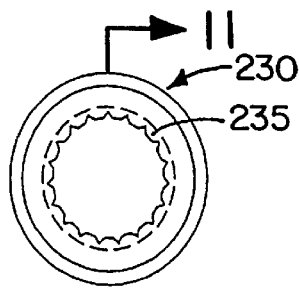
FIG. 13 is an axial elevational view of the coupling device of FIG. 11 taken from position 13 in FIG. 11.

As shown in FIGS. 11, 12 and 13, a splined coupling 230 is provided. FIG. 11 is a longitudinal cross-sectional view, taken at line 11—11 of the splined coupling 230 shown in FIG. 13. FIG. 12 is an axial cross-sectional view, taken at line 11—11 of the splined coupling shown in FIG. 11, and FIG. 13 is an axial elevational view of the coupling device of FIG. 11 taken from position 13 in FIG. 11. The splined coupling 230 is adapted to receive the splined segment 228 of the lower portion 220.

The splined coupling 230 includes a shallow recess 232, a coupling splined segment 234, a plurality of splines 235, a stop plug 236, and a deep recess 238. The shallow recess 232 is formed by a wall 240. The deep recess 238 is formed by the wall 242. In use, the splined segment 228 of the lower section 220 is inserted into the shallow recess 232, and the splined segment 228 is received by the coupling splined segment 234 in an interlocking, relatively tight fit. The splines 235 of the coupling splined segment 234 are machined to match in number and size the splines 229 on the splined segment 228 of the lower section 220. When the respective splined segments 228 and 234 are interlocked, the coupling 230 cannot be rotated with respect to the lower section 220.

Figure 14:
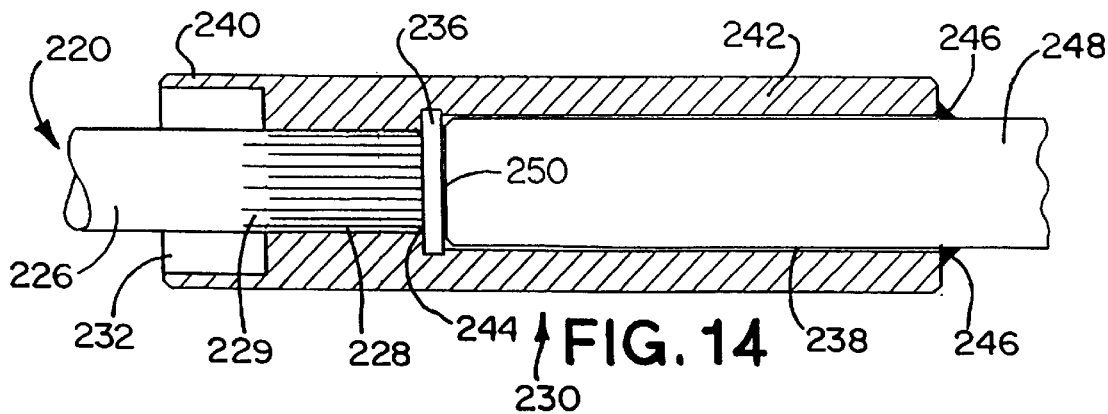
FIG. 14 is a longitudinal cross-sectional view of a splined coupling with a splined lower segment inserted and an upper segment welded in place.

As best shown in FIG. 14, when the splined segments are fully interlocked, the lower section end 244 comes in contact with and is stopped by the stop plug 236. The stop plug 236 acts to prevent over-insertion of the lower segment into the splined coupling 230. When the splined segments 228 and 234 are interlocked, the wall 240 of the shallow recess 232 acts as a skirt to cover a small portion of the lower section near the splined segment 228. The skirting effect of the wall 240 helps to avoid entry of contaminants into parts of the coupling such as the splined segment 234, which would be difficult to clean and sterilize.

The number of splines in the two splined segments should match so that the maximum number of possible interlocking positions are enabled. While it is possible to have different numbers of splines but still have successful interlocking, for example 24 splines mating with, e.g., 12 splines, such is not preferred. Preferably, in both the splined segment 228 of the lower section, and in the coupling splined segment 234 of the coupling 230, there are at least 12 splines. More preferably, in each splined segment there are 19 splines. The preferred 19 splines result in 18 possible alignments of the two splined segments.

The preferred 18 possible alignments of the lower portion and the upper portion of the vertically extending support provide a wide range of possible positions from which the surgeon can select to position the ratcheting lifting device 24. This advantage is particularly suitable and helpful for the less-invasive mid-cab procedure. As discussed above, the variability in position of the internal mammary artery requires great flexibility on the part of the surgeon in access that artery for dissection and harvest. Thus, the surgeon is provided with a surgical support apparatus for a ratcheting lifting device with which the angle of retraction can be closely controlled over a very wide range. Since the splined connection is maintained by the interlocking of the splines and the force of gravity alone, it is quite easy for the surgeon or a surgical assistant to change the angle of the upper section of the vertically extending support during the course of a surgical procedure. By means of the splined coupling, by which the exact angle at which the retraction apparatus is suspended with respect to the patient's body may be selected and reliably retained without the possibility of slippage. The splined coupling provides for adjustment of the angle during the course of a surgical procedure, thereby allowing the surgeon to better adapt to the changing conditions and needs of the patient.

Referring again to FIG. 14, in the preferred embodiment of the present invention, the splined coupling 230 is preferably welded by a weld 246 to an upper section 248 (partially shown in FIG. 14). Preferably, the weld 246 is smooth and continuous around the circumference of the upper section 248 and the coupling 230, and is free of seams, cracks, pinholes or other openings into which contaminants could become lodged. As shown in FIG. 14, preferably the upper section 248 extends fully into the deep recess 238, and the lower end 250 of the upper section 248 is in contact with the stop plug 236 when the weld 246 is made.

Preferably the upper section 248 of the present embodiment, above the weld 246, is essentially identical to the upper section 154 described in reference to FIG. 5. The description of the upper section 154 applies equally to the upper section 248. Thus, the upper section 248 includes horizontal extensions which are made from metal stock which is square in cross-section. Preferably, the stock is about ½ inch by ½ inch square (about 12.5 mm×12.5 mm). In coordination therewith, preferably the both clamps such as the clamps 150 and the ratcheting lifting devices 24 include a square opening of appropriately matching size so that such clamps and the devices 24 can be easily and reliably mounted on the horizontal extensions of the present invention. Thus, for example, as described with reference to the clamp 150 and the device 24, the opening in any device used on the horizontal extension of the upper section of the present embodiment may be approximately 12.6 mm square, to accommodate some slight variation in the size of the cross bar member, but to avoid any excess freedom of movement. It is noted that while the preferred stock is square, other configurations may be used, such as triangular, pentagonal, hexagonal, or rectangular for example. Furthermore, when a term such as "square" is used, this refers to the overall cross-sectional shape, rather than to a perfectly square (or other) cross-section. Thus, a square stock may have slightly rounded corners, for example, and still be considered square.

Preferably the splines 229 and 235 on the respective splined segments 228 and 234 are involute. In the embodiment shown in FIG. 10, the key-like splined portion 228 is disposed on the upwardly-directed end of the lower portion of the support member. Alternatively, the key-like splined segment may be disposed on the downwardly-directed upper portion of the support member, although such an embodiment would not provide the contamination-avoiding benefit of the downwardly-oriented skirt formed by the wall 240 and the recess 232.

The following describes various methods by which the splined connection may be put to use in a surgical procedure. The steps are generally outlined, and are not intended to limit the many uses to which the invention may be put.

In one embodiment, the present invention provides a method of providing surgical retraction to a patient positioned relative to a support platform, including the steps of: (1) mounting upper and lower portions of a support member with respect to each other by a lock-and-key-like splined connection and with respect to the platform; (2) positioning a lifting device above the patient by mounting the lifting device with respect to the upper portion of the support member; and (3) applying retraction to the patient. In one embodiment, the lock-and-key-like splined connection includes a key-like splined portion and a lock-like splined portion whereby the upper portion and the lower portion may be matingly interconnected. In one embodiment, the upper portion further includes a horizontally extending portion. In one embodiment, the step of mounting further includes selecting a desired angle of orientation between the horizontally extending portion and the support platform. In one embodiment, the step of mounting further includes mounting the upper portion to the lower portion by matingly interconnecting the key-like splined portion to the lock-like spined portion at the desired angle. In one embodiment, the step of mounting further includes attaching the lower portion to an anchoring receptacle on the support platform.

In one embodiment, the present invention provides a method of providing surgical retraction to a patient positioned relative to a support platform, including the steps of: (1) positioning a lifting device above the patient, said positioning including mounting the lifting device by a multiple part generally vertically extending support member which has a lock-and-key-like splined connection between at least two of the multiple parts; and (2) adjusting the position of the lifting device relative to the patient by selecting an angular relation between a first one of the parts and a second one of the parts at the lock-and-key-like splined connection; and (3) applying retraction to the patient.

In one embodiment, the present invention provides a method of mounting a surgical retractor with respect to a patient support platform, including the steps of: (1) mounting with respect to the platform a vertically extending support member which has a lower portion, an upper portion, and a lock-and-key-like splined connection for connecting the lower portion to the upper portion; (2) connecting the lower portion to the upper portion by inserting a key-like splined portion into a lock-like splined portion; and (3) mounting the surgical retractor on the vertically extending support member. In one embodiment, the upper portion further includes a horizontally extending portion. In one embodiment, the step of connecting further includes selecting a desired angle of orientation between the horizontally extending portion and the patient. In one embodiment, the step of connecting further includes mounting the upper portion to the lower portion by matingly interconnecting the key-like splined portion to the lock-like spined portion at the desired angle. In one embodiment, the step of mounting further includes attaching the lower portion to an anchoring receptacle on the support platform.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

What is claimed is:

1. A generally vertically extending support member for a surgical retraction apparatus, comprising
   a lower portion of the support member having a rectilinear portion for insertion into an anchoring receptacle;
   an upper portion of the support member having a horizontally extending portion; and
   a splined coupling adaptor for connecting together the lower and upper portions, wherein the adaptor comprises a splined segment having a key-like splined portion and a lock-like splined portion.

2. A support member as in claim 1, wherein the splines are involute.

3. A support member as in claim 1 wherein the key-like splined portion is disposed on the lower portion of the support member.

4. A support member as in claim 1 wherein the key-like splined portion is disposed on the upper portion of the support member.

5. A support member as in claim 1 wherein each splined segment comprises at least 10 teeth.

6. A support member as in claim 1 wherein each splined segment comprises at least 19 teeth.

7. A support member as in claim 3 wherein the lock-like splined portion is disposed in a downwardly disposed sleeve-like coupling on the upper portion of the vertical support member.

8. A support member as in claim 1 wherein by means of the splined coupling adaptor the horizontally extending portion of the upper may be securely aligned at a selected angle with respect to the anchoring receptacle.

9. The support member of claim 1, further comprising an extender bar, the extender bar comprising an extender bar portion, a clamp portion, and a first receptacle for receiving a horizontal support bar from the horizontally extending portion, wherein the receptacle is disposed at approximately right angles to the horizontal support bar and the clamp is positioned to retain the horizontal support bar in the receptacle.

10. A method of providing surgical retraction to a patient positioned relative to a support platform, comprising the steps of:
    mounting upper and lower portions of a support member with respect to each other by a lock-and-key-like splined connection and with respect to the platform;
    positioning a lifting device above the patient by mounting the lifting device with respect to the upper portion of the support member; and
    applying retraction to the patient.

11. A method as in claim 10, wherein the lock-and-key-like splined connection comprises a key-like splined portion and a lock-like splined portion whereby the upper portion and the lower portion may be matingly interconnected.

12. A method as in claim 10, wherein the upper portion further comprises a horizontally extending portion.

13. A method as in claim 12, wherein the step of mounting further comprises selecting a desired angle of orientation between the horizontally extending portion and the support platform.

14. A method as in claim 13 wherein the step of mounting further comprises mounting the upper portion to the lower portion by matingly interconnecting the key-like splined portion to the lock-like spined portion at the desired angle.

15. A method as in claim 10, wherein the step of mounting further comprises attaching the lower portion to an anchoring receptacle on the support platform.

16. The method of claim 10, further comprising the step of mounting with respect to the support member an extender bar.

17. A method of providing surgical retraction to a patient positioned relative to a support platform, comprising the steps of:
    positioning a lifting device above the patient, said positioning comprising mounting the lifting device by a multiple part generally vertically extending support member which has a lock-and-key-like splined connection between at least two of the multiple parts; and
    adjusting the position of the lifting device relative to the patient by selecting an angular relation between a first one of the parts and a second one of the parts at the lock-and-key-like splined connection; and
    applying retraction to the patient.

18. A method of mounting a surgical retractor with respect to a patient support platform, comprising the steps of:
    mounting with respect to the platform a vertically extending support member which has a lower portion, an upper portion, and a lock-and-key-like splined connection for connecting the lower portion to the upper portion;

connecting the lower portion to the upper portion by inserting a key-like splined portion into a lock-like splined portion; and mounting the surgical retractor on the vertically extending support member.

19. A method as in claim 18, wherein the upper portion further comprises a horizontally extending portion.

20. A method as in claim 19, wherein the step of connecting further comprises selecting a desired angle of orientation between the horizontally extending portion and the patient.

21. A method as in claim 20 wherein the step of connecting further comprises mounting the upper portion to the lower portion by matingly interconnecting the key-like splined portion to the lock-like spined portion at the desired angle.

22. A method as in claim 18, wherein the step of mounting further comprises attaching the lower portion to an anchoring receptacle on the support platform.

* * * * *